(12) United States Patent
Washburn et al.

(10) Patent No.: US 10,758,214 B2
(45) Date of Patent: Sep. 1, 2020

(54) BIOPSY DEVICE AND METHOD

(71) Applicant: UVision360, Inc., Research Triangle Park, NC (US)

(72) Inventors: Scott Washburn, Durham, NC (US); Erich Dreyer, Durham, NC (US); Allison London Brown, Durham, NC (US); David Robinson, Schaumburg, IL (US); Brad Jacobs, Durham, NC (US)

(73) Assignee: UVision360, Inc., Raleigh, NC (US)

( * ) Notice: Subject to any disclaimer, the term of this patent is extended or adjusted under 35 U.S.C. 154(b) by 13 days.

(21) Appl. No.: 15/885,097

(22) Filed: Jan. 31, 2018

(65) Prior Publication Data

US 2019/0142400 A1 May 16, 2019

Related U.S. Application Data

(60) Provisional application No. 62/585,221, filed on Nov. 13, 2017.

(51) Int. Cl.
| | |
|---|---|
| *A61B 10/04* | (2006.01) |
| *A61B 10/02* | (2006.01) |
| *A61B 1/07* | (2006.01) |
| *A61B 1/018* | (2006.01) |
| *A61B 1/00* | (2006.01) |

(Continued)

(52) U.S. Cl.
CPC .............. *A61B 10/04* (2013.01); *A61B 1/07* (2013.01); *A61B 10/0275* (2013.01); *A61B 1/00094* (2013.01); *A61B 1/015* (2013.01); *A61B 1/018* (2013.01); *A61B 1/0669* (2013.01); *A61B 2010/0216* (2013.01)

(58) Field of Classification Search
CPC ....... A61B 10/04; A61B 1/07; A61B 10/0275; A61B 1/015; A61B 1/00094; A61B 1/018; A61B 1/0669; A61B 2010/0216
See application file for complete search history.

(56) References Cited

U.S. PATENT DOCUMENTS

| | | |
|---|---|---|
| 5,231,989 A | 8/1993 | Middleman et al. |
| 5,483,951 A | 1/1996 | Frassica et al. |
| 5,611,769 A | 3/1997 | Monroe |

(Continued)

FOREIGN PATENT DOCUMENTS

| | | |
|---|---|---|
| CA | 2593731 C | 1/2015 |
| DE | 19752430 A1 | 7/1999 |

(Continued)

*Primary Examiner* — Rene T Towa
(74) *Attorney, Agent, or Firm* — Mintz Levin Cohn Ferris Glovsky and Popeo, P.C.

(57) ABSTRACT

Various biopsy devices configured to biopsy tissue from a body cavity and methods of use are provided. In an exemplary embodiment, a biopsy sleeve is provided with an elongate shaft having distal and proximal ends. The elongate shaft is configured to receive at least a portion of an imaging device therein, and an engagement member is disposed on the proximal end and configured to engage with the imaging device. A biopsy collector is engageable with the elongate shaft and is configured to collect tissue for a biopsy sample. At least part of the distal end of the elongate shaft is configured to allow visualization therethrough using the imaging device such that a user can visualize the tissue being collected.

31 Claims, 9 Drawing Sheets

(51) Int. Cl.
*A61B 1/06* (2006.01)
*A61B 1/015* (2006.01)

(56) References Cited

U.S. PATENT DOCUMENTS

| | | |
|---|---|---|
| 5,823,940 A | 10/1998 | Newman |
| 5,961,486 A | 10/1999 | Twardowski et al. |
| 6,110,103 A | 8/2000 | Donofrio |
| 6,371,909 B1 | 4/2002 | Hoeg et al. |
| 6,419,626 B1 * | 7/2002 | Yoon ............... A61B 1/00052 600/103 |
| 6,482,169 B1 | 11/2002 | Kuhle |
| 6,572,631 B1 | 6/2003 | McCartney |
| 6,749,580 B2 | 6/2004 | Work et al. |
| 6,761,684 B1 | 7/2004 | Speier |
| 6,863,651 B2 | 3/2005 | Remijan et al. |
| 6,958,035 B2 | 10/2005 | Friedman et al. |
| 7,008,401 B2 | 3/2006 | Thompson et al. |
| 7,029,467 B2 | 4/2006 | Currier et al. |
| 7,233,820 B2 | 6/2007 | Gilboa |
| 7,776,005 B2 | 8/2010 | Haggstrom et al. |
| 7,815,564 B2 | 10/2010 | Geitz et al. |
| 7,921,848 B2 | 4/2011 | Nikolchev et al. |
| 8,079,364 B2 | 12/2011 | Lowe et al. |
| 8,251,975 B2 | 8/2012 | Atkins et al. |
| 8,460,182 B2 | 6/2013 | Ouyang et al. |
| 8,532,747 B2 | 9/2013 | Nock et al. |
| 8,814,846 B2 | 8/2014 | Horton et al. |
| 8,834,357 B2 | 9/2014 | Oskin et al. |
| 8,845,522 B2 | 9/2014 | McIntyre et al. |
| 8,961,452 B2 | 2/2015 | Purdy |
| 9,011,412 B2 | 4/2015 | Albritton, IV et al. |
| 9,039,649 B2 | 5/2015 | Neisz et al. |
| 9,370,650 B2 | 6/2016 | Hanson et al. |
| 9,855,021 B2 | 1/2018 | Abraham |
| 2002/0137984 A1 | 9/2002 | Chhibber et al. |
| 2005/0049459 A1 | 3/2005 | Hern |
| 2005/0096642 A1 | 5/2005 | Appling et al. |
| 2005/0272975 A1 | 12/2005 | McWeeney et al. |
| 2005/0283048 A1 * | 12/2005 | Gill ............... A61B 1/00059 600/121 |
| 2006/0149186 A1 | 7/2006 | Wantink et al. |
| 2007/0118019 A1 | 5/2007 | Mitani et al. |
| 2007/0129605 A1 | 6/2007 | Schaaf |
| 2007/0167682 A1 | 7/2007 | Goldfarb et al. |
| 2007/0197871 A1 | 8/2007 | Geitz et al. |
| 2008/0076966 A1 * | 3/2008 | Isaacson ............... A61B 1/303 600/106 |
| 2008/0154091 A1 | 6/2008 | Dejima et al. |
| 2008/0167527 A1 | 7/2008 | Slenker et al. |
| 2008/0249366 A1 | 10/2008 | Gruber et al. |
| 2009/0054728 A1 * | 2/2009 | Trusty ............... A61B 1/00135 600/114 |
| 2009/0076498 A1 | 3/2009 | Saadat et al. |
| 2009/0299336 A1 | 12/2009 | Jay-Robinson |
| 2010/0016757 A1 | 1/2010 | Greenburg et al. |
| 2010/0145142 A1 | 6/2010 | Begemann et al. |
| 2010/0249513 A1 | 9/2010 | Tydlaska |
| 2010/0261967 A1 | 10/2010 | Pacey et al. |
| 2010/0280368 A1 | 11/2010 | Can et al. |
| 2010/0305503 A1 | 12/2010 | Fang et al. |
| 2010/0331883 A1 | 12/2010 | Schmitz et al. |
| 2011/0071349 A1 | 3/2011 | Drontle et al. |
| 2011/0276113 A1 * | 11/2011 | Cybulski ............... A61B 18/042 607/101 |
| 2011/0319718 A1 | 12/2011 | Hakanen et al. |
| 2012/0016260 A1 | 1/2012 | To |
| 2012/0143006 A1 | 6/2012 | Avitsian et al. |
| 2012/0259406 A1 | 10/2012 | Schreck et al. |
| 2012/0289858 A1 * | 11/2012 | Ouyang ............... A61B 10/0275 600/562 |
| 2013/0053645 A1 * | 2/2013 | Weitzner ............ A61B 1/00135 600/121 |
| 2013/0281782 A1 | 10/2013 | Zhou |
| 2014/0107416 A1 | 4/2014 | Birnkrant |
| 2014/0200402 A1 | 7/2014 | Snoke et al. |
| 2014/0357955 A1 | 12/2014 | Avitsian et al. |
| 2015/0112132 A1 * | 4/2015 | Nieman ............... A61M 25/0147 600/109 |
| 2015/0202089 A1 | 7/2015 | Campbell et al. |
| 2015/0320406 A1 * | 11/2015 | Sethi ............... A61B 10/0283 600/565 |
| 2015/0374221 A1 * | 12/2015 | Sahney ............ A61B 1/00135 600/104 |
| 2016/0066770 A1 * | 3/2016 | Barbato ............ A61B 1/00071 600/138 |
| 2017/0055813 A1 | 3/2017 | London Brown et al. |
| 2017/0273716 A1 * | 9/2017 | Garofalo ............ A61B 17/3423 |
| 2018/0071481 A1 | 3/2018 | Snoke et al. |
| 2018/0199797 A1 | 7/2018 | London Brown et al. |
| 2019/0231177 A1 | 8/2019 | Dreyer et al. |

FOREIGN PATENT DOCUMENTS

| | | |
|---|---|---|
| DE | 19752430 C2 | 5/2000 |
| DE | 10045036 C1 | 7/2002 |
| WO | 2017/087579 A1 | 5/2017 |
| WO | 2019/094948 A1 | 5/2019 |

* cited by examiner

BIOPSY DEVICE AND METHOD

FIELD

Devices, methods, and systems of taking a tissue biopsy are provided herein.

BACKGROUND

Minimally invasive surgeries, diagnostic procedures, exploratory procedures, and other medical procedures have been favored more and more by patients and physicians given the improved healing times and the less invasive nature of the operations. Various medical devices and instrumentation have been developed to accomplish these operations, such as medical introducers, imaging devices such as fiber Optic scopes, and other related endoscopic devices.

Minimally invasive surgeries can also include tissue biopsies. However, accurately and efficiently taking a tissue biopsy through a minimally invasive procedure, such as by using a curette, can prove challenging for a variety of factors, such as accessibility of the tissue to be biopsied and lack of visualization at the biopsy site. For example, curettes are often used to biopsy tissue. However, use of a curette requires physicians to operate without any means of visualization. In an exemplary operation, a curette can be inserted into a body cavity, such as a uterus, of a patient through use of feel and experience of the physician. A distal tip of the curette can be scraped along tissue, such as uterine tissue, to collect a biopsy sample. This procedure is often done without visualization or with inconvenient and intrusive visualization means that increase the complication of the procedure.

Accordingly, there remains a need for improved devices, methods, and systems of taking a tissue biopsy.

SUMMARY

Devices, methods, and systems of taking a tissue biopsy are provided herein. In one embodiment, a biopsy sleeve is provided that includes an elongate shaft having distal and proximal ends, a lumen extending therebetween, and a longitudinal axis extending therealong. The lumen is configured to receive at least a portion of an imaging device therein. An engagement member is positioned on the proximal end of the elongate shaft, and it is configured to engage with the imaging device. A biopsy collector is positioned adjacent to the distal end of the elongate shaft, and the biopsy collector is configured to collect tissue for a biopsy sample. At least part of the distal end of the elongate shaft is configured to allow imaging therethrough using the imaging device such that a user can visualize the tissue being collected.

The biopsy sleeve can vary in numerous ways. For example, the biopsy sleeve can also include a suction port that is configured to apply suction through the lumen of the elongate shaft and to the biopsy collector. The distal end of the elongate shaft can also be sealed, and the proximal end of the elongate shaft can be open and configured to receive at least a portion of the imaging device therethrough. In another example, the biopsy collector can include an opening into the lumen of the elongate shaft that is configured to receive tissue samples therethrough. The biopsy collector can also have at least one cutting surface thereon that is configured to cut tissue samples. In other embodiments, the elongate shaft can have an angled distal region that is angled at a non-zero angle relative to the longitudinal axis of the elongate shaft. For example, the angled distal region can be angled at approximately 15 degrees relative to the longitudinal axis of the elongate shaft. In another example, the engagement member can be configured to prevent relative movement between the biopsy sleeve and the imaging device. The engagement member can also have a plurality of engagement features extending proximally therefrom that are configured to clip onto the imaging device.

In another aspect, a biopsy system is provided that includes a biopsy sleeve with an elongate shaft having distal and proximal ends and a lumen extending therebetween. The biopsy sleeve has an engagement member positioned on the proximal end of the elongate shaft, and the biopsy sleeve has a biopsy collector positioned adjacent to the distal end of the elongate shaft that is configured to collect tissue for a biopsy sample. The biopsy system also includes an imaging device with a handle and an elongate imaging member extending distally from the handle. The elongate imaging member is configured to be inserted into the lumen of the elongate shaft of the biopsy sleeve and is configured to take images therefrom, and the handle is configured to engage with the engagement member of the biopsy sleeve.

In various embodiments, at least a portion of the biopsy sleeve can be configured to allow imaging therethrough by the imaging device. The biopsy sleeve can also include a suction port configured to apply suction to tissue collected by the biopsy collector. The biopsy sleeve can also have a fluid port configured to deliver fluid through the lumen of the elongate shaft. In another example, when the biopsy sleeve and the imaging device are engaged by the engagement member, the elongate imaging member can have a distalmost position in the lumen of the biopsy sleeve that is proximal to the biopsy collector. In another embodiment, the engagement member can be configured to prevent relative movement between the biopsy sleeve and the imaging device. In one example, the engagement member can have a plurality of engagement features extending proximally therefrom that are configured to clip onto the imaging device. The biopsy collector can include an opening into the lumen of the elongate shaft configured to receive tissue samples therethrough. In another embodiment, the elongate shaft of the biopsy sleeve can have an angled distal region that is angled at a non-zero angle relative to a longitudinal axis of the elongate shaft. The imaging device can also be a Complementary Metal-Oxide Semiconductor fiberscope.

In another aspect, a method of collecting a biopsy sample is provided that includes positioning a biopsy sleeve adjacent to tissue to be sampled using images taken by an imaging device disposed at least partially in the biopsy sleeve such that the imaging device visualizes the tissue through the biopsy sleeve. The method also includes collecting a tissue sample using a biopsy collector positioned at or adjacent to a distal end of the biopsy sleeve.

The method can have numerous variations. For example, the method can also include engaging the biopsy sleeve with the imaging device by inserting an elongate imaging member of the imaging device into an elongate shaft of the biopsy sleeve until a distal end of the elongate imaging member is positioned proximal to the biopsy collector and an engagement member of the biopsy sleeve fixedly engages with a handle of the imaging device. The method can also include applying suction to the biopsy collector by connecting a suction device to a suction port of the biopsy sleeve. In still another example, the method can also include after collecting the tissue sample by the biopsy collector, removing the biopsy sleeve from the body cavity using images from the imaging device to guide removal.

In another aspect, a biopsy sleeve is provided that includes an elongate shaft with distal and proximal ends, at least one lumen extending therebetween, and a longitudinal axis extending therealong. The lumen is configured to receive at least a portion of an imaging device therein. An engagement member is positioned on the proximal end of the elongate shaft and is configured to engage with the imaging device. A biopsy collector is movably disposed within the elongate shaft and is configured to extend from the distal end of the elongate shaft and collect tissue for a biopsy sample therefrom. At least part of the distal end of the elongate shaft is configured to allow imaging therethrough using the imaging device such that a user can visualize the tissue being collected.

The biopsy sleeve can vary in numerous ways. For example, the biopsy collector can include a brush. The brush can include a brush head at a distal end thereof, a handle at a proximal end thereof, and a brush shaft that is configured to be longer than the elongate shaft. The biopsy sleeve can also include a port configured to allow insertion and removal of the biopsy collector from the elongate shaft. In another example, the distal end of the elongate shaft can be open and configured to allow the biopsy collector to extend therefrom to collect tissue. The biopsy sleeve can also include an opening in the elongate shaft that is configured to allow the biopsy collector to extend therefrom to collect tissue. In one embodiment, the biopsy sleeve can include a plurality of lumens extending through the elongate shaft. At least one of the plurality of lumens can be configured to receive the biopsy collector therethrough, and at least one other of the plurality of lumens can be configured to receive the imaging device therein. The biopsy sleeve can also include a suction port configured to apply suction through the lumen of the elongate shaft. The biopsy sleeve can also have a fluid port configured to deliver fluid through the lumen of the elongate shaft. In one example, the biopsy sleeve can include an opening in the elongate shaft that has at least one cutting surface thereon configured to cut tissue samples. In another example, the elongate shaft can have an angled distal region that is angled at a non-zero angle relative to the longitudinal axis of the elongate shaft. The engagement member can also be configured to prevent relative movement between the biopsy sleeve and the imaging device. The imaging device can also include a Complementary Metal-Oxide Semiconductor fiberscope. In another example, the elongate shaft can be flexible, and in still another example, the elongate shaft can be rigid. At least part of the distal end of the elongate shaft can be made of an optically clear material such that imaging of the imaging device occurs directly through the elongated shaft. In one example, the biopsy sleeve can include an opening in the distal end of the elongate shaft such that imaging of the imaging device occurs through the opening.

In another aspect, a biopsy system includes a biopsy sleeve with an elongate shaft that has distal and proximal ends and at least one lumen extending therebetween. The biopsy sleeve has an engagement member positioned on the proximal end of the elongate shaft, and the biopsy sleeve has a biopsy collector with a first position and a second position. A distal end of the biopsy collector is entirely contained within the elongate shaft in the first position, and the distal end of the biopsy collector extends distally from the elongate shaft to collect tissue for a biopsy sample in the second position. The biopsy collector is movable between the first and second positions. The system includes an imaging device with a handle and an elongate imaging member that extends distally from the handle. The elongate imaging member is configured to be inserted into the lumen of the elongate shaft of the biopsy sleeve and is configured to take images therefrom. The handle is configured to engage with the engagement member of the biopsy sleeve.

In one embodiment, the biopsy collector of the system can be slidably and removably positioned within the elongate shaft. In another example, the biopsy collector can include a brush. The brush can include a brush head at a distal end thereof, a handle at a proximal end thereof, and a brush shaft that is configured to be longer than the elongate shaft. The biopsy system can include a port that is configured to allow insertion and removal of the biopsy collector from the elongate shaft. The distal end of the elongate shaft can be open and configured to allow the biopsy collector to extend therefrom to collect tissue. The biopsy system can include an opening in the elongate shaft that is configured to allow the biopsy collector to extend therefrom to collect tissue. In one example, the biopsy system can include a plurality of lumens extending through the elongate shaft. At least one of the plurality of lumens can be configured to receive the biopsy collector therethrough, and at least one of the plurality of lumens can be configured to receive the imaging device therein. At least a portion of the biopsy sleeve can be configured to allow imaging therethrough by the imaging device. The biopsy sleeve can also include a suction port configured to apply suction to the biopsy sleeve. In another example, the engagement member can be configured to prevent relative movement between the biopsy sleeve and the imaging device. In one example, the imaging device can include a Complementary Metal-Oxide Semiconductor fiberscope. The imaging device can include an elongated member that has optical fiber throughout the elongated member to provide light for viewing. The imaging device can also include an internal light source configured to transmit light down the optical fiber located within the elongated member.

In another aspect, a method of collecting a biopsy sample can be provided that includes positioning a biopsy sleeve adjacent to tissue to be sampled using images taken by an imaging device disposed at least partially in the biopsy sleeve. The imaging device visualizes the tissue through the biopsy sleeve. The method also includes collecting a tissue sample using a biopsy collector extending beyond a distal end of the biopsy sleeve.

The method can include a number of different embodiments. In one example, the method can also include, prior to collecting the tissue sample, inserting the biopsy collector through a port in the biopsy sleeve, sliding the biopsy collector through the biopsy sleeve, and extending the biopsy collector distally beyond the distal end of the biopsy sleeve. In another example, the method can include, after collecting the tissue sample, retracting the biopsy collector proximally into the biopsy sleeve such that at least a distal end of the biopsy collector is entirely within the biopsy sleeve. The method can further include, after collecting the tissue sample by the biopsy collector, removing the biopsy sleeve from the body cavity using images from the imaging device to guide removal. In one embodiment, the method can include engaging the biopsy sleeve with the imaging device by inserting an elongate imaging member of the imaging device into an elongate shaft of the biopsy sleeve until at least a distal end of the elongate imaging member is positioned within the biopsy sleeve and an engagement member of the biopsy sleeve fixedly engages with a handle of the imaging device.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

When attempting to biopsy tissue, especially in a non-invasive way, physicians are often required to remove tissue that is difficult to access and accurately extract. This problem is exacerbated in situations where a biopsy must be performed inside a body cavity of a patient without any simple means of visualization, such as extracting uterine tissue. Thus, various biopsy sleeves are provided herein that are configured to engage with various medical imaging devices that can be advanced into a patient and perform a biopsy with accompanying imaging from the imaging devices, providing users a way to quickly extract tissue for biopsies that is both minimally invasive and accurate. While biopsy sleeves are described herein in connection with fiberscopes and uterine tissue, the biopsy sleeves can be used with a variety of types of imaging devices and can be used to biopsy a variety of types of tissue, or in other surgical applications.

In an exemplary embodiment, a biopsy sleeve is provided with an elongate shaft having distal and proximal ends. The elongate shaft is configured to receive at least a portion of an imaging device therein, and an engagement member is disposed on the proximal end and configured to engage with the imaging device. At least part of the distal end of the elongate shaft is configured to allow visualization therethrough using the imaging device such that a user can visualize tissue being collected. A biopsy collector is engageable with the elongate shaft and is configured to collect tissue for a biopsy sample. For example, in one embodiment, a biopsy collector can be disposed adjacent to the distal end and can be configured to collect tissue for a biopsy sample. In another embodiment, a biopsy collector can be removably and/or movably disposed within the elongate shaft and can be configured to extend from the distal end of the elongate shaft to collect tissue for a biopsy sample therefrom.

FIGS. 1-4 illustrate one embodiment of a biopsy sleeve 100 with an imaging device 500. The biopsy sleeve 100 includes an elongate shaft 102 with an engagement member 120 and a biopsy collector 140. The elongate shaft 102 has a proximal end 104, a distal end 106, and a lumen extending therebetween. The proximal end 104 is open, and the lumen is configured to receive at least part of the imaging device 500 therealong. The lumen has an internal diameter D1 that is greater than a diameter of at least part of the imaging device 500. In one embodiment, the internal diameter D1 of the elongate shaft 102 can be configured to be larger than the diameter of at least part of the imaging device 500 such that biopsy samples can travel down the lumen of the elongate shaft 102 while the imaging device 500 is still disposed in the elongate shaft 102. The elongate shaft 102 is configured to allow imaging and/or visualization therethrough by the imaging device 500. For example, at least part of the elongate shaft 102 can be at least partially transparent, for example it can have a transparent distal end 106. While the elongate shaft 102 illustrated herein uses transparency to allow imaging therethrough, imaging can be accomplished in a variety of different ways. In other embodiments, an opening can be formed in the elongate shaft 102 to allow imaging directly through the opening, such as an opening at the distal-most end of the elongate shaft. In some embodiments, the imaging device 500 can extend to the opening to provide imaging therethrough. Alternatively, various clear and/or transparent slides, lenses, members, etc. can be positioned, embedded, formed, etc. in an outer surface of the elongate shaft 102 to allow imaging therethrough without creating additional openings. The elongate shaft 102 can be flexible or rigid depending on the desired use of the sleeve 100, and the distal end 106 of the elongate shaft 102 can either be sealed or open. The elongate shaft 102 can be made of a variety of materials, such as Polyether ether ketone (PEEK), High-density polyethylene (HDPE), Polytetrafluoroethylene (PTFE), Polyether block amide (PEBA) such as PEBAX, other thermoplastic elastomers (TPE), and/or Stainless Steel with any combination of polymers. The elongate shaft 102 also has the engagement member 120 disposed on the proximal end 104 thereof.

Figure 1:
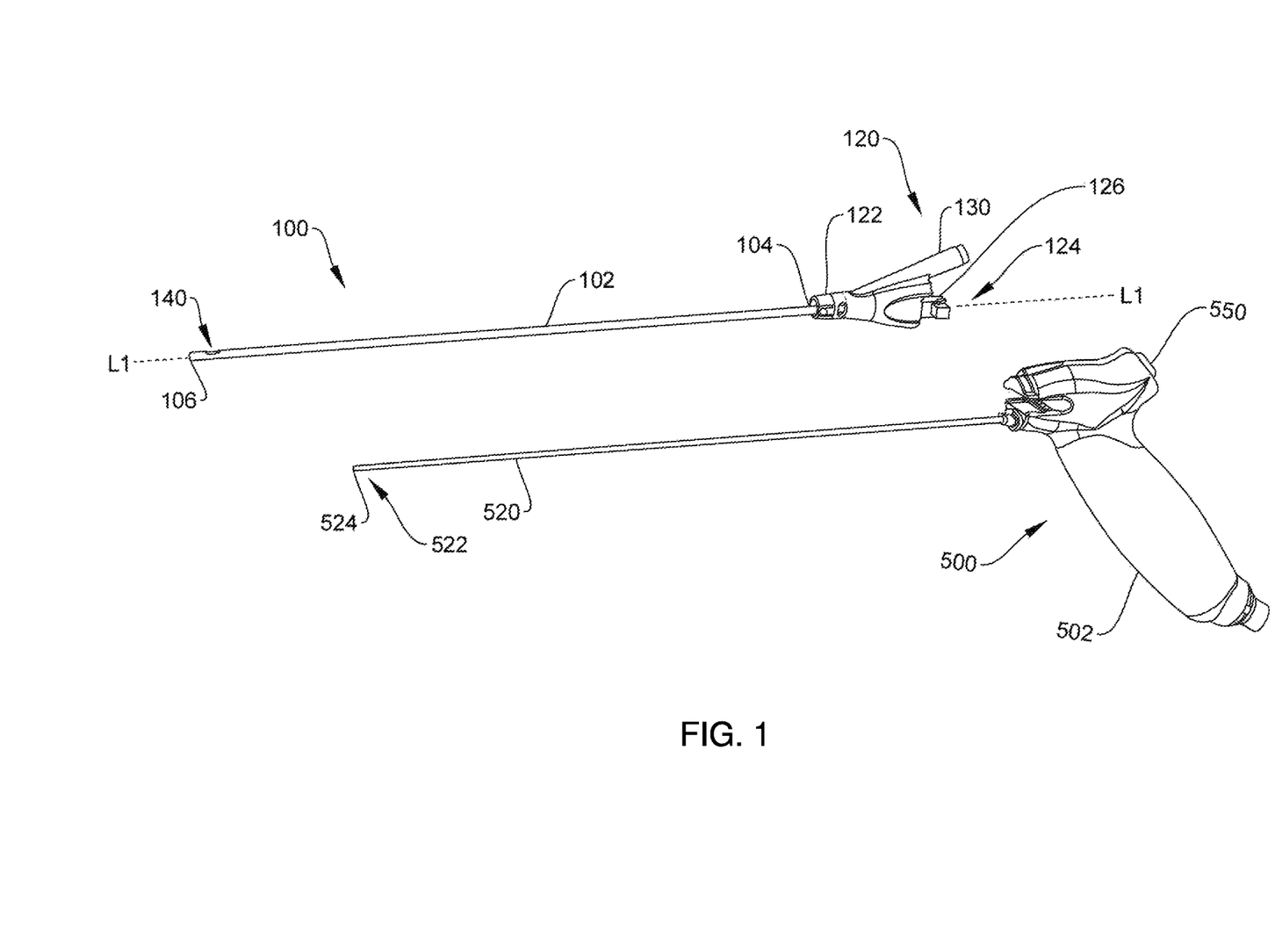
FIG. 1 is a perspective view of one embodiment of a biopsy sleeve with an imaging device.
Figure 2:
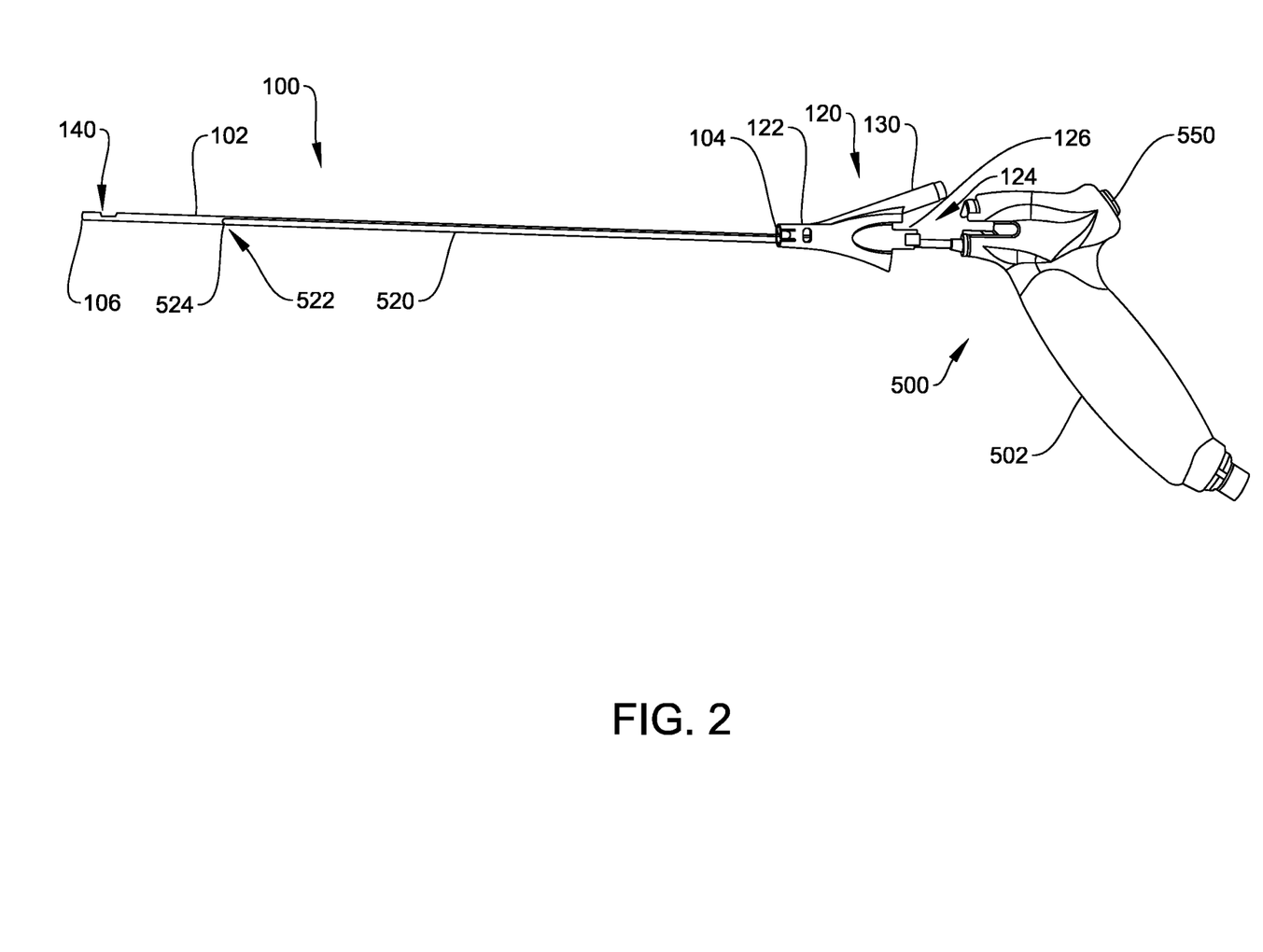
FIG. 2 is a perspective view of the biopsy sleeve on the imaging device of FIG. 1.
Figure 3:
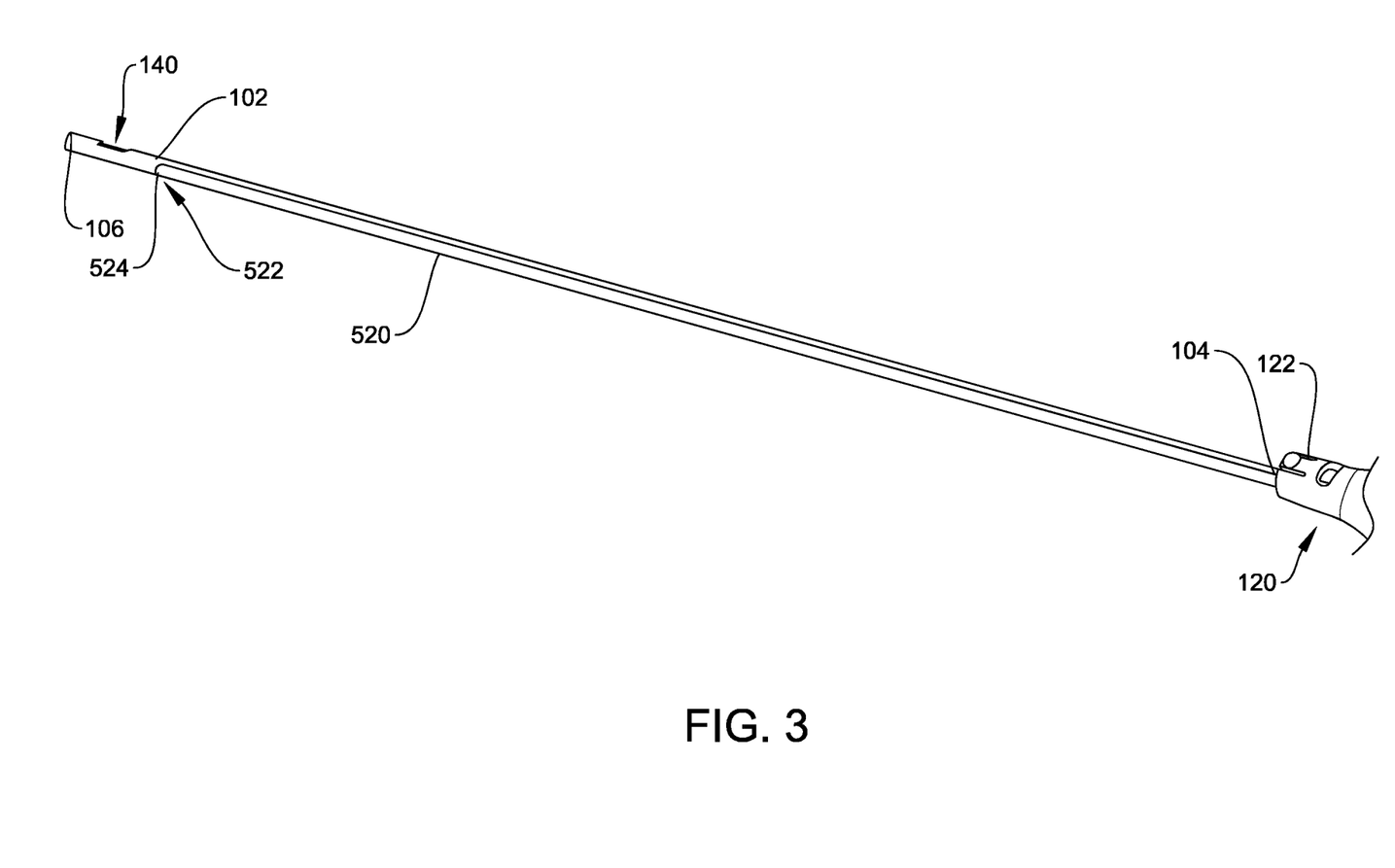
FIG. 3 is a perspective view of a distal end of the biopsy sleeve on the imaging device of FIG. 1.

The engagement member 120 is configured to engage the elongate shaft 102 on a distal end 122 thereof and is configured to engage with the imaging device 500 on a proximal end 124 thereof. The engagement member 120 is configured to receive at least part of the imaging device 500 therethrough such that at least part of the imaging device 500 can pass entirely therethrough and into the lumen of the elongate shaft 102. In some embodiments, the engagement member 120 is configured to secure the imaging device 500 with respect to the elongate shaft 102 such that the imaging device 500 is fixably disposed in a distal position within the elongate shaft 102, as illustrated in FIG. 3, and the imaging device 500 is non-slidable relative to and non-rotatable about a longitudinal axis L1 thereof within the elongate shaft 102. As illustrated, the engagement member 102 includes one or more engagement fingers 126 configured to engage corresponding features on the imaging device 500, for example in snap or friction fit engagements. The fingers 126 are configured to be engaged or disengaged by a user, such that the biopsy sleeve 100 is removably, non-rotatably, and non-slidably affixed to the imaging device 500. While fingers 126 are illustrated, a variety of engagement features can be used, such as seals, clips, posts, locks, etc. While the sleeve 100 as illustrated is non-rotatable relative to the imaging device 500 when the engagement member is engaged, other embodiments can be provided with rotation means configured to rotate the sleeve 100 relative to the imaging device 500 without disengaging the sleeve 100 from the imaging device 500, for example by utilizing a rotation knob around the engagement member 120.

Additionally a suction port 130 additionally is associated with the engagement member 120. The suction port 130 is configured to connect to the lumen of the elongate shaft 102 and is configured to provide suction thereto, for example to draw tissue into the elongate shaft through the biopsy collector 140. While the suction port 130 is illustrated as extending from the engagement member 120, the suction port 130 can connect anywhere on the elongate shaft 102 such that the suction port 130 can apply suction thereto. The suction port 130 is shown to have a luer fitting, but any fitting can be used that provides a sealable opening for suction. The suction port 130 can also be configured to allow fluid flow therethrough to provide irrigation to a target site. However, other embodiments can provide an additional port for fluid inflow. The ports described herein can take the form of various seals, ports, engagements, Leur fittings, etc. and can connect to various fluid lines, suction tubes, IV lines, syringes, etc.

Figure 4:
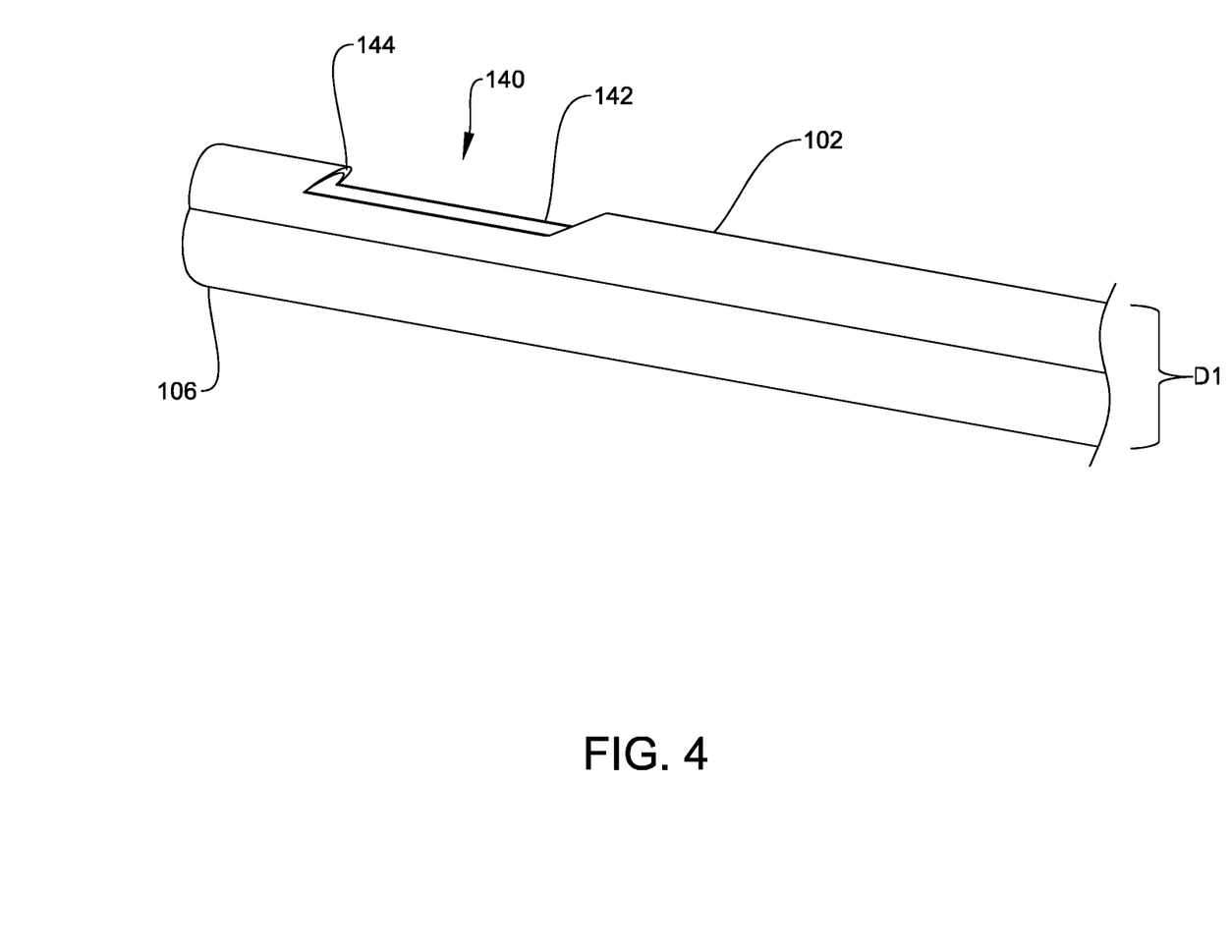
FIG. 4 is a perspective view of a distal tip of the biopsy sleeve of FIG. 1.

Opposite to the engagement member 120 and adjacent to the distal end 106 of the elongate shaft 102 is the biopsy collector 140, as illustrated in FIG. 4. The biopsy collector 140 is configured to engage tissue thereon and sever tissue samples such that suction can draw the tissue samples through the biopsy collector 140 and into the elongate shaft 102. The biopsy collector 140 can take a variety of forms, such as an opening 142 through the elongate shaft 102 in an approximately rectangular shape. One or more cutting surfaces 144, such as a triangular tooth as illustrated in FIG. 4, are disposed thereon and configured to engage and cut tissue to collect biopsy tissue samples. The triangular tooth of the cutting surface 144 is positioned in the opening 142, facing proximally, and is configured to cut tissue upon proximal movement of the elongate shaft 102 along tissue. While a distinct opening for the biopsy collector 140 is illustrated herein, in other embodiments the biopsy collector 140 can be incorporated into the distal end 106 of the elongate shaft 102. For example, the distal end 106 of the elongate shaft 102 can include the biopsy collector 140 such that the distal end 106 can be open and have one or more cutting surfaces therearound. As suction is applied to the elongate shaft 102, the combined distal end 106 and biopsy collector 140 can be configured to draw tissue therein using suction and cut one or more tissue samples due to the cutting surfaces. Additionally, the biopsy collector 140 is not limited to openings in the elongate shaft 102 and in other embodiments can be graspers, cutters, scissors, needles, curettes, etc. The sleeve 100 can be configured to be disposable after a single use or reusable.

The sleeve 100 can be engaged with the imaging device 500, similar to the devices illustrated in U.S. Patent App. Pub. No. 2017/0055813 to London Brown, et al., filed on Oct. 5, 2016 and U.S. Provisional Patent App. No. 62/585,221 to London Brown, et al., filed on Nov. 13, 2017, both of which are incorporated herein by reference in their entireties. The imaging device 500 has a handle 502 and an elongate imaging member 520 extending distally from the handle 502. The handle 502 includes a light source disposed within the handle 502.

The elongate imaging member 520 extends from the handle 502 and is configured to be inserted through the engagement member 120 and into the elongate shaft 102. While a distal portion 522 of the elongate imaging member 520 terminates proximal to the biopsy collector 140, in other embodiments the elongate imaging member 520 can extend past the biopsy collector 140 and terminate distal to the biopsy collector 140 or anywhere in between the distal end 106 and the proximal end 104 of the elongate shaft 102. For example, the elongate imaging member 520 can extend to approximately the distal end 106 of the elongate shaft 102 and provide imaging therefrom, such as through an opening formed in the elongate shaft 102. The elongate imaging member 520 includes an imaging unit 524 engaged on the distal portion 522 of the elongate imaging member 520. The imaging unit 524 can take a variety of forms, such as an active-pixel sensor array or a Complementary Metal-Oxide Semiconductor (CMOS) sensor, as provided in more detail in U.S. Patent App. Pub. No. 2017/0055813. The imaging unit 524 is configured to be in communication with the handle 502 and is configured to obtain images of areas adjacent thereto with assistance from a plurality of light transmission devices.

The plurality of light transmission devices extend from the light source in the handle 502, extend through a lumen defined by the elongate imaging member 520, and terminate at respective distal ends thereof disposed about the distal portion 522 of the elongate imaging member 520. The light transmission devices are arranged about the imaging unit 524. The light transmission devices are configured to receive the light from the light source and to transmit the light to the distal ends thereof to provide light to the area adjacent to the imaging unit 524 such that images can be taken within a body cavity of a patient. The light transmission devices can include fiber optic elements or light delivery fibers, and can be rigid or flexible to allow for bending or flexing within the elongate shaft 102.

The imaging device 500 is also configured to connect to a power source. For example, a power source can be disposed in the handle 502, or the power source can be external to the device and connected to the handle 502. The power source is arranged to be in electrical communication with the light source in the handle 502. A communication element 550 can also be operably engaged with the handle 502 such that the communication element 550 is in signal communication with the imaging unit 524 and configured to receive an image signal therefrom associated with an image captured by the imaging unit 524 or to communicate electrical power to the imaging unit 524. In addition, a display device for displaying the image, or a computer device for storing or analyzing the image, can be in communication with the communication element 550 via a wired communication arrangement or a wireless communication arrangement. All connections provided herein can be either wired or wireless connections.

In use, a user engages the sleeve 100 with the imaging device 500 by inserting the elongate imaging member 520 into the elongate shaft 102 until the imaging unit 524 is positioned in a distal-most position that is proximal to the biopsy collector 140 and the engagement member 120 of the sleeve 100 engages with the handle 502 of the imaging device 500. The user then inserts the distal end 106 of the sleeve 100 into a body cavity of a patient and positions the biopsy collector 140 adjacent to tissue to be biopsied using images taken by the imaging device 500 to ensure correct placement of the sleeve 100. The user can actuate suction by connecting a suction device (not shown) to the suction port 130. However, the suction device can be connected at a variety of times, for example before inserting the sleeve 100 into a patient. When suction has been actuated and the biopsy collector 140 is positioned based on imaging from the imaging device 500, the user draws tissue into the biopsy collector 140 using suction, and the user moves the cutting surfaces 144 back and forth across tissue to sever a tissue sample and draw the tissue sample into the elongate shaft 102. For example, the user can move the biopsy collector 140 distally, engage suction, and then draw the biopsy collector 140 proximally to draw tissue against the cutting surface 144 and biopsy the tissue. When a tissue sample has been collected, the user removes the sleeve 100 from the body cavity, using images obtained from the imaging device 500 to guide removal if needed.

Figure 5:
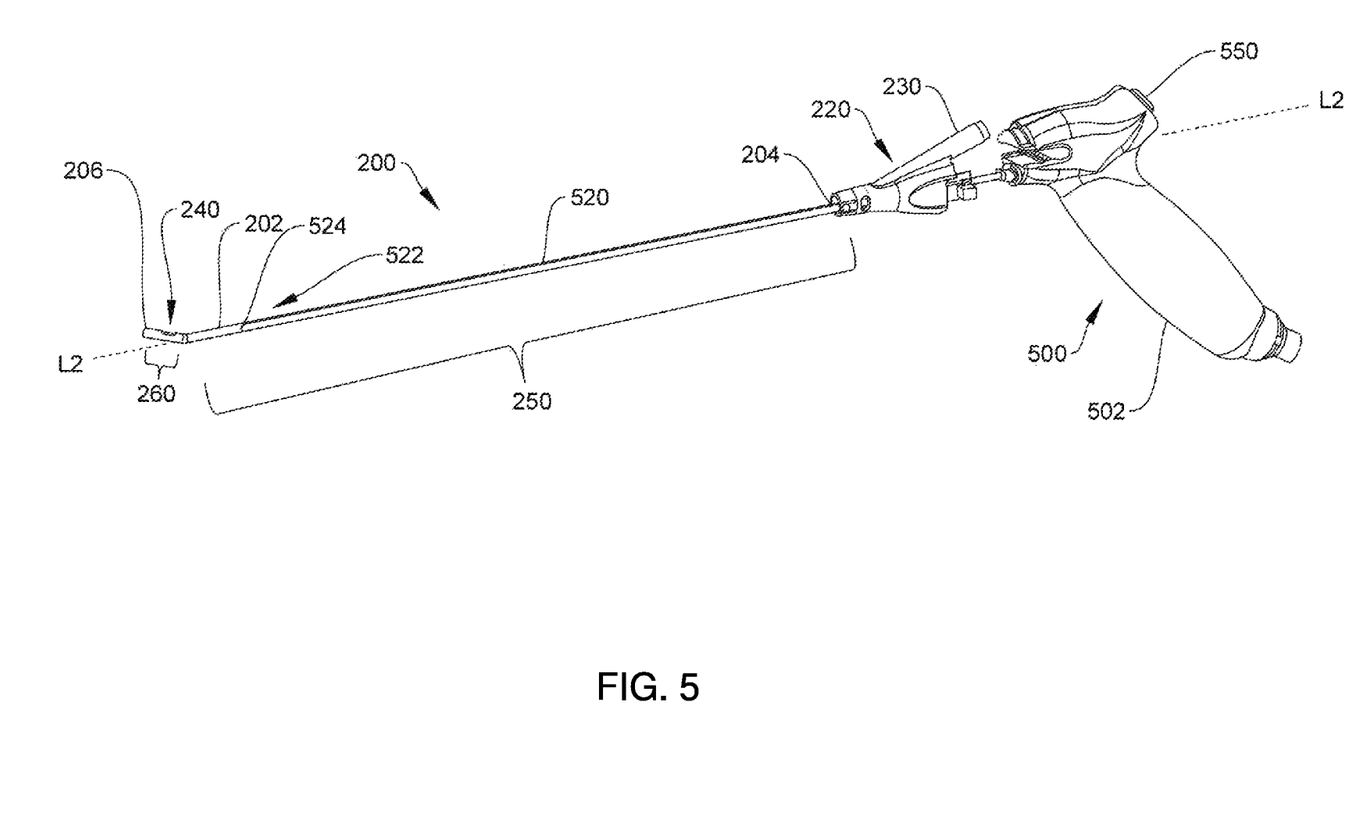
FIG. 5 is a perspective view of another embodiment of a biopsy sleeve with an imaging device.
Figure 6:
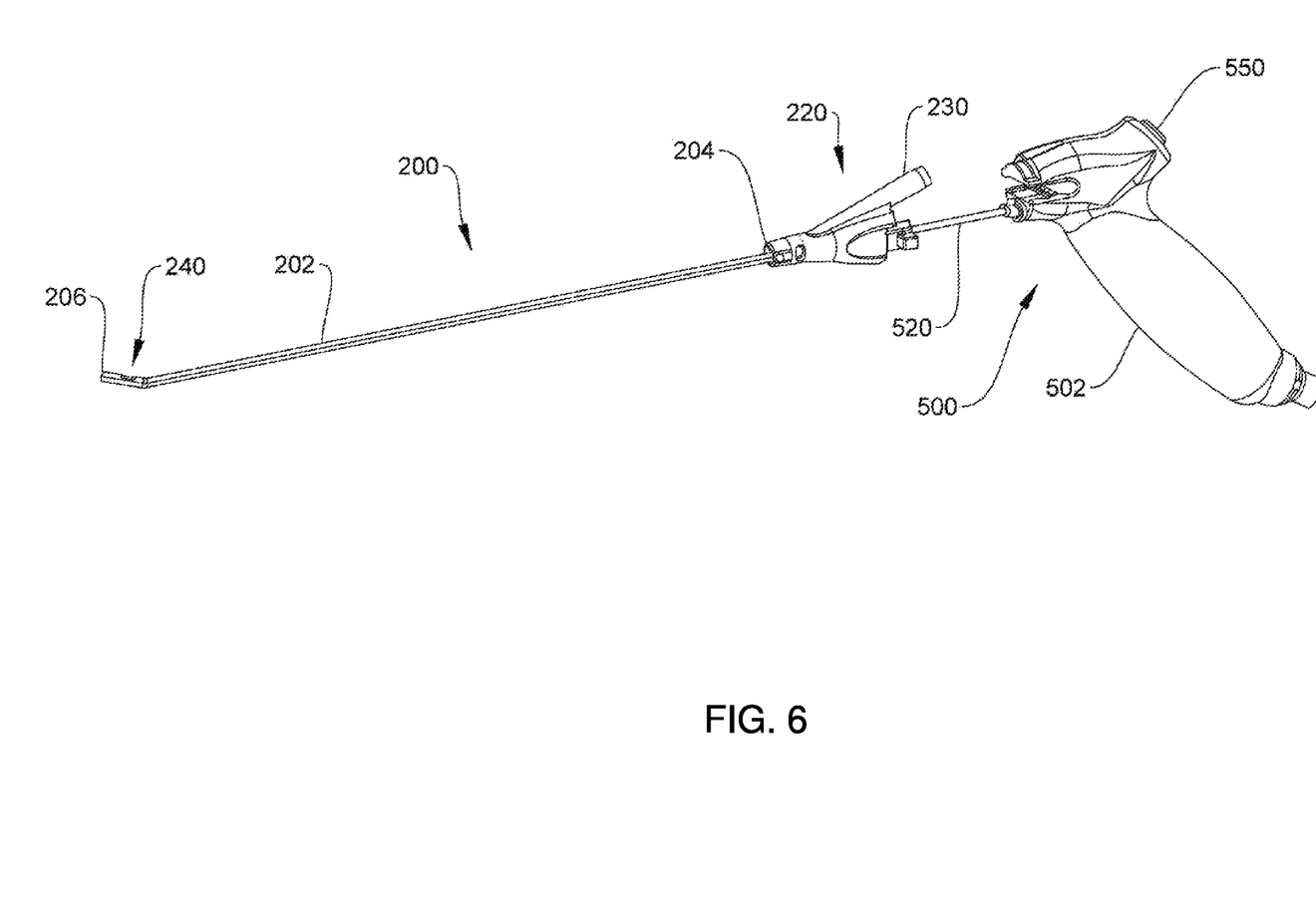
FIG. 6 is a line drawing of the biopsy sleeve on the imaging device of FIG. 5.
Figure 7:
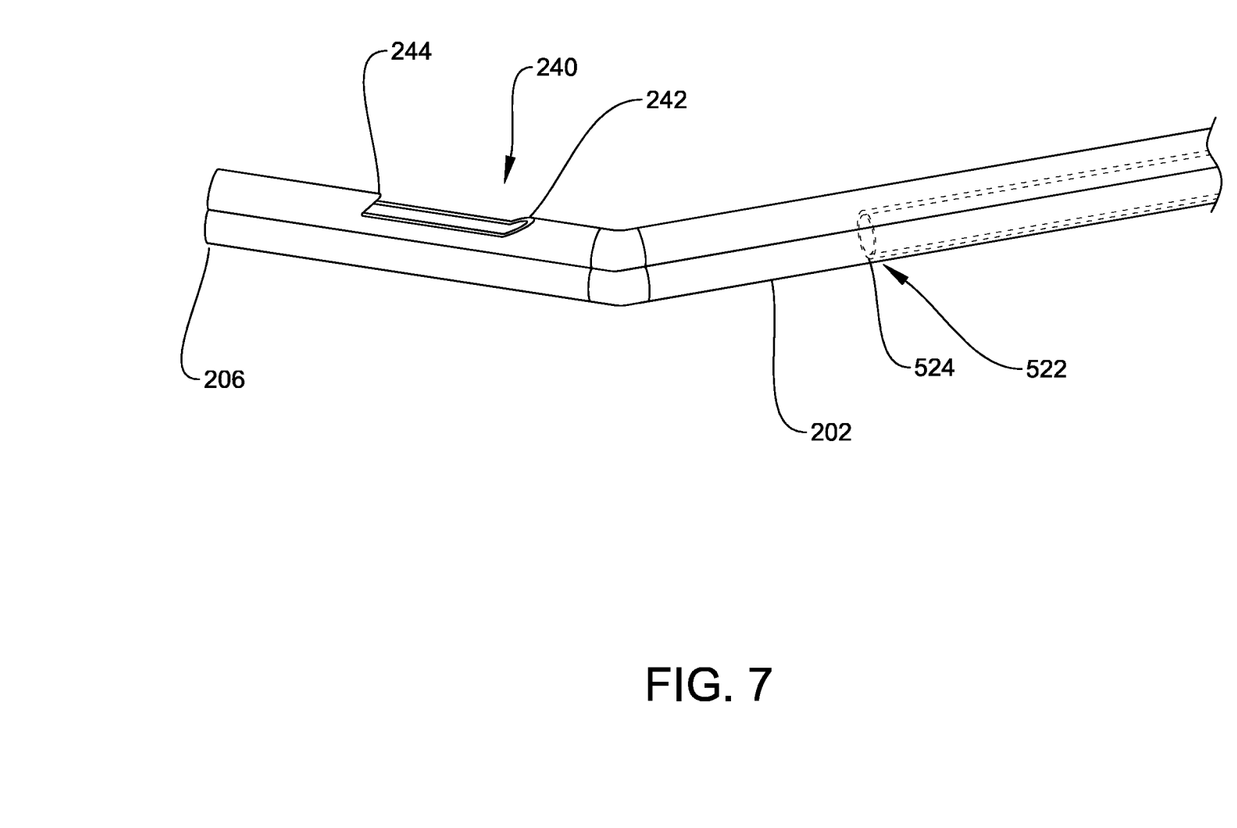
FIG. 7 is a transparent line drawing of distal ends of the biopsy sleeve and the imaging device of FIG. 5.

A variety of different embodiments of the sleeve 100 are possible. For example, FIGS. 5-7 illustrate another embodiment of a sleeve 200 that has a curved shaft 202 instead of a straight shaft such as the elongate shaft 102 of the sleeve 100. However, the sleeve 200 is otherwise similar to the sleeve 100. The sleeve 200 includes the curved shaft 202 with an engagement member 220, a suction port 230, and a biopsy collector 240. The curved shaft 202 has a proximal end 204, a distal end 206, and a lumen extending therebetween. The proximal end 204 is open, and the lumen is configured to receive at least part of an imaging device therein, such as the imaging device 500 or other imaging devices. The curved shaft 202 has a straight proximal region 250 and an angled distal region 260, and the straight proximal region 250 is configured to receive at least part of the imaging device therein.

The angled distal region 260 can be angled at between 0 and 30 degrees, such as 15 to 20 degrees, relative to a longitudinal axis L2 extending through the straight proximal region 250. The angled distal region 260 includes the biopsy collector 240 and is configured to provide a greater range of motion when a user maneuvers the biopsy collector 240 to collect tissue samples. The distal-most end of the angled distal region 260 can either be open or closed, similar to the sleeve 100. The curved shaft 202 is configured to allow imaging therethrough by the imaging device 500. For example, at least part of the curved shaft 202 can be at least partially transparent, such as the angled distal region 260. The curved shaft 202 is configured to receive the elongate imaging member 520 therein, with the imaging unit 524 terminating proximal to the angled distal region 260. However, in other embodiments, imaging devices can be received that extend into the angled distal region 260.

The biopsy collector 240 is disposed entirely on the angled distal region 260 and can take a variety of forms, such as an opening 242 through the curved shaft 202 with one or more cutting surfaces 244 formed by the triangular tooth as illustrated in FIG. 7. As with the biopsy collector 140, the biopsy collector 240 is not limited to the opening illustrated, however. The sleeve 200 can be configured to be disposable after a single use or reusable.

In use, the sleeve 200 is manipulated in the same way as the sleeve 100, with a user engaging the sleeve 200 and the imaging device 500, inserting the distal end 206 of the sleeve 200 into a body cavity of a patient and positioning the biopsy collector 240 adjacent to tissue to be sampled using images from the imaging device 500, and using suction and cutting surfaces 244 to collect one or more biopsy samples at an exact location due to the images taken by the imaging device 500. However, the sleeves disclosed herein are not limited to including a suction port and/or one or more cutting surfaces.

Figure 8:
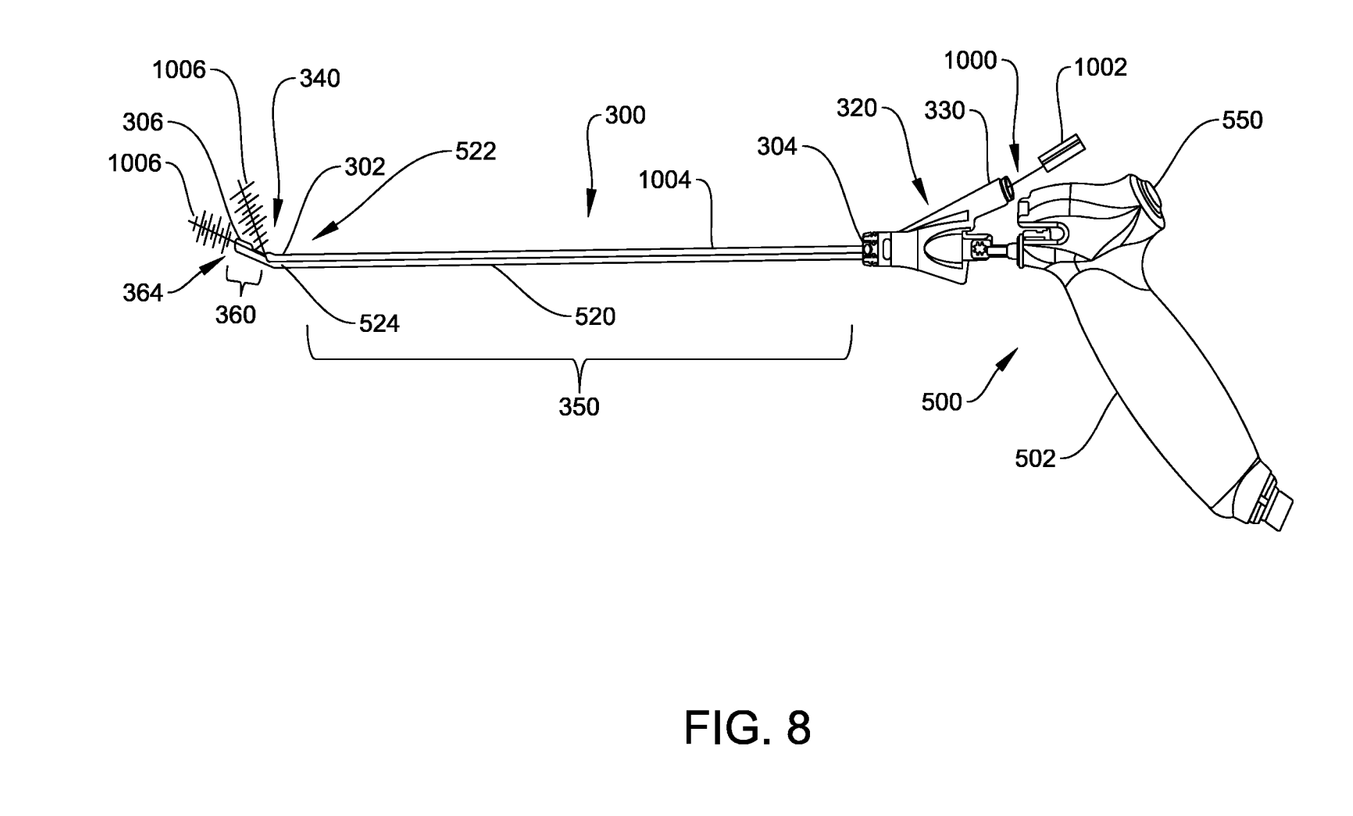
FIG. 8 is a transparent line drawing of another embodiment of a biopsy sleeve on the imaging device of FIG. 5.
Figure 9:
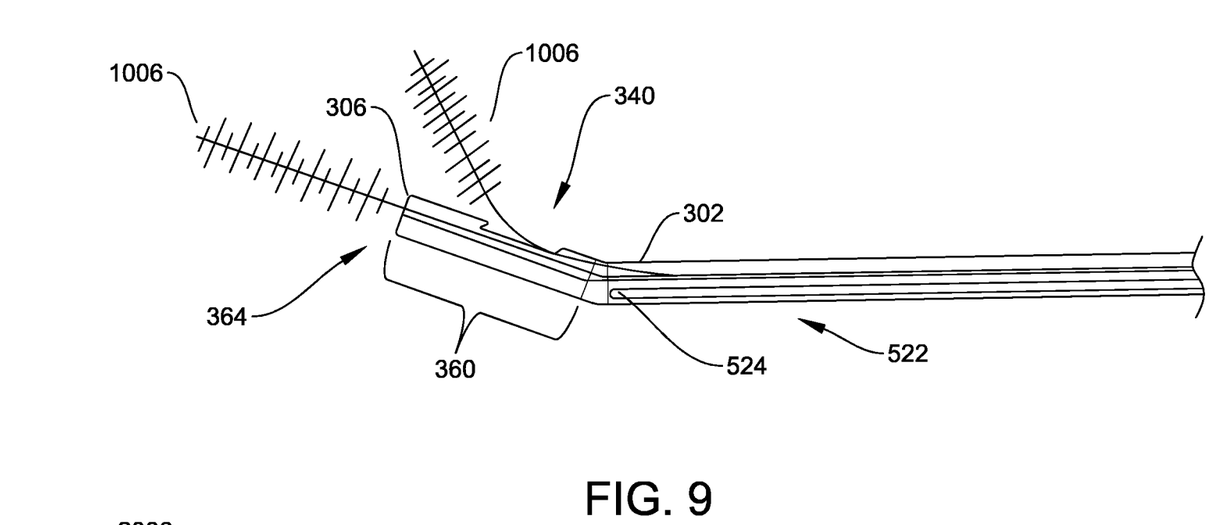
FIG. 9 is a transparent line drawing of distal ends of the biopsy sleeve of FIG. 8 and the imaging device of FIG. 5.

While using suction and one or more cutting surfaces represent one approach to collecting a biopsy sample, a variety of different approaches are possible. For example, FIGS. 8-9 illustrate another embodiment of a sleeve 300 that has a curved shaft 302. The sleeve 300 is similar to the sleeves 100, 200 discussed above. The curved shaft 302 has a proximal end 304, a distal end 306, and a lumen extending therebetween. The proximal end 304 is open, and the lumen is configured to receive at least part of an imaging device therein, such as the imaging device 500 or other imaging devices. The curved shaft 302 has a straight proximal region 350 and an angled distal region 360, and the straight proximal region 350 is configured to receive at least part of the imaging device therein.

The angled distal region 360 can be angled at between 0 and 30 degrees, such as 15 to 20 degrees. The angled distal region 360 includes an opening 340, and the distal-most end 364 of the angled distal region 360 is open. However, in other embodiments, the distal-most end can be closed. The curved shaft 302 is configured to allow imaging therethrough by the imaging device 500, either through the material itself by using optically clear material or by an opening therethrough and/or a viewing window embedded therein. For example, at least part of the curved shaft 302 can be at least partially transparent, such as the angled distal region 360. The curved shaft 302 is configured to receive the elongate imaging member 520 therein, with the imaging unit 524 terminating proximal to the angled distal region 360. However, in other embodiments, imaging devices can be received that extend into the angled distal region 360.

Similar to the sleeve 200, the sleeve 300 includes the curved shaft 302 with an engagement member 320, a hub or port 330, and the opening 340. However, the port 330 on the sleeve 300 is configured to receive a biopsy collector, such as an elongate brush 1000, therein. The opening 340 is configured to allow the brush 1000 to pass therethrough to access a target site distal to the sleeve 300. The port 330 is not a suction port, but some embodiments can incorporate both a suction port and a brush port to provide suction to the sleeve and provide access to a target site for the brush. Other embodiments can incorporate both suction and brush access into one engagement hub or port, and the one or more ports can be additionally configured to allow fluid flow therethrough to provide irrigation to a target site. Still other embodiments can provide a separate port for fluid inflow. The ports described herein can take the form of various seals, ports, engagements, Leur fittings, etc. and can connect to various fluid lines, suction tubes, IV lines, syringes, etc. Additionally, the opening 340 does not have any cutting surfaces thereon, but some embodiments can incorporate both an opening with one or more cutting surfaces and a brush to allow tissue samples to be severed by the cutting surfaces and/or to be collected by a brush.

The elongate brush 1000 includes a handle 1002 on a proximal end, an elongate shaft 1004, and a brush head 1006 including a plurality of bristles on a distal end thereof. The brush 1000 is sufficiently long that it can be inserted into the port 330, travel entirely through the sleeve 300, and extend out the distal end 306 of the sleeve 300 with the handle 1002 still protruding proximally from the port 330. The brush head 1006 is configured to be rubbed along or made to contact a target tissue area. As the brush head 1006 contacts the target tissue area, the brush head 1006 is configured to collect tissue samples thereon and be retracted back into the sleeve 300. The brush head 1006 has bristles thereon, but various heads can be used, such as protrusions, hooks, scrubbing members, etc. The brush 1000 can be made from a variety of materials, such as Polyether ether ketone (PEEK), High-density polyethylene (HDPE), Polytetrafluoroethylene (PTFE), Polyether block amide (PEBA) such as PEBAX, other thermoplastic elastomers (TPE), and/or various metals such as Stainless Steel with any combination of polymers. The handle 1002, the elongate shaft 1004, and the brush head 1006 can each be made of different materials or one or more of the same materials. Each component of the brush 1000 can be manufactured individually or can be of a unitary construction.

As illustrated in FIGS. 8 and 9, the brush 1000 can exit the sleeve 300 on the distal end thereof out of either the opening 340 or the distal-most end 364 of the angled distal region 360, both of which are open and are configured to allow the brush head 1006 to pass therethrough. However, in other embodiments, either the distal-most end of the angled distal region can be closed or the opening can be removed, thus allowing the brush 1000 to exit through only one distal opening. The sleeve 300 can be configured to be disposable after a single use or reusable. The brush 1000 can also be used with a sleeve having a straight shaft instead of an angled shaft.

In use, the sleeve 300 is manipulated in the same way as the sleeve 100, with a user engaging the sleeve 300 and the imaging device 500, inserting the distal end 306 of the sleeve 300 into a body cavity of a patient and positioning the opening 340 and/or the distal-most end 364 adjacent to tissue to be sampled using images from the imaging device 500. In this embodiment, the brush 1000 is inserted through the port 330 and along the sleeve 300 to the tissue to be sampled. The brush 1000 can be inserted at any time before, during, or after insertion of the sleeve 300 into the body cavity. The brush head 1006 is rubbed or scraped against the tissue to be sampled by a user manipulating the handle 1002 and the sleeve 300 as needed. Sample tissue is collected in the brush head 1006, and a user then withdraws the brush head 1006 with the samples back into the sleeve 300. The user can optionally additionally apply suction, irrigation, and/or cut samples using one or more cutting surfaces, as discussed above.

Figure 10:
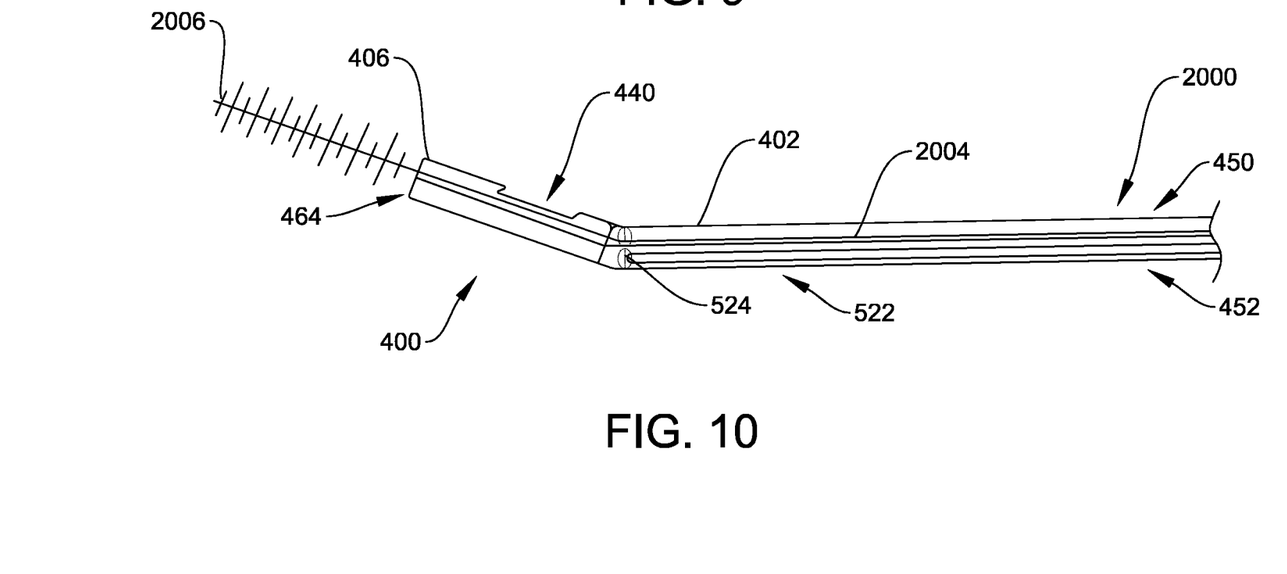
FIG. 10 is a transparent line drawing of a distal end of another embodiment of a biopsy sleeve on the imaging device of FIG. 5.

Thus the brush, suction, and/or one or more cutting surfaces can all be integrated together into one device, allowing a user to choose whether to collect samples using the brush, suction, and/or cutting surfaces. Additionally, the sleeves can incorporate the brushes in a variety of ways. The sleeve 300 discussed above had a single lumen therethrough, which was shared between the brush 1000 and the imaging device 500. However, in other embodiments, there can be a plurality of lumens in the sleeve that can incorporate the brush and/or the imaging device. For example, FIG. 10 illustrates another sleeve 400 similar to the sleeve 300 discussed above. The sleeve 400 has a shaft 402 with a proximal end (not shown) and a distal end 406. The proximal end is open, and the shaft 402 is configured to receive at least part of an imaging device, such as the imaging device 500 or other imaging devices. The shaft 402 has an opening 440 and a distal-most end 464 that is also open, but in other embodiments one or more of these openings can be closed. The shaft 402 is configured to allow imaging therethrough by the imaging device 500, either through the material itself by using optically clear material or by an opening therethrough and/or a viewing window embedded therein. As with the sleeve 300, the sleeve 400 is configured to receive an elongate brush 2000 therein, and the opening 440 is configured to allow the brush 2000 to pass therethrough to access tissue for a biopsy sample distally from the sleeve 400. The elongate brush 2000 is similar to the brush 1000 and includes a handle on a proximal end, an elongate shaft 2004, and a brush head 2006 including a plurality of bristles on a distal end thereof. The brush head 2006 is configured to collect biopsy samples at a target tissue area.

However, as illustrated in FIG. 10, the shaft 402 has a plurality of lumens therethrough, such as a brush lumen 450 and an imaging lumen 452. The brush lumen 450 is configured to receive the brush 2000 therein, and the imaging lumen 452 is configured to receive an imaging device, such as the imaging device 500, therein. The brush 2000 thus extends along the dedicated brush lumen 450 and exits the sleeve 400 on the distal end thereof out of either the opening 440 or the distal-most end 464 of the shaft 402. The imaging lumen 452 can have an opening therethrough on its distal end or can be entirely sealed on its distal end, only allowing insertion of an imaging device at its proximal end. In other embodiments, the shaft can have one or more additional lumens, for example a working channel lumen and one or two fluid lumens such as a fluid inflow lumen and a fluid outflow lumen.

The sleeves discussed above are removable from any associated imaging device, but embodiments can incorporate both the sleeves and the imaging devices into a fully reusable device such that an imaging device, such as the imaging device 500, is fully and permanently incorporated into the design of one or more of the sleeves discussed above. Thus the imaging device would effectively incorporate a sleeve therearound with one or more lumens therethrough, such as a working channel lumen, a viewing lumen, one or more fluid flow lumens, etc. The one or more lumens of the imaging device could have open distal end(s), closed distal end(s), or a combination of the two.

The sleeves disclosed herein can be provided in any of a variety of sizes, depending on patient anatomy, procedure type, imaging device to be used, and various other parameters which will be readily apparent to one having ordinary skill in the art. The sleeves can also have a variety of lengths, for example, about 15 cm to 30 cm, and can have a variety of diameters, such as about 1 mm to 5 mm. The sleeves can further be flexible or rigid depending on the conditions under which the sleeves will be used and the surgical tool(s) that will be used with the sleeves, for example the imaging device(s), and they can be made from a variety of materials, such as Polyether ether ketone (PEEK), High-density polyethylene (HDPE), Polytetrafluoroethylene (PTFE), Polyether block amide (PEBA) such as PEBAX, other thermoplastic elastomers (TPE), and/or various metals such as Stainless Steel with any combination of polymers.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components with which the devices will be used, and the methods and procedures in which the devices will be used. The figures provided herein are not necessarily to scale. Although the devices and methods disclosed herein are generally directed to surgical techniques, they can also be used in applications outside of the surgical field. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A biopsy system, comprising:
a biopsy sleeve including an elongate shaft having distal and proximal ends and at least one lumen extending therebetween, the biopsy sleeve having an engagement member positioned on the proximal end of the elongate shaft, and the biopsy sleeve having a biopsy collector positioned adjacent to the distal end of the elongate shaft and configured to collect tissue for a biopsy sample; and
an imaging device including a handle and an elongate imaging member integral therewith and extending distally from the handle, the elongate imaging member being configured to be inserted into and removed from the lumen of the elongate shaft of the biopsy sleeve, the elongate imaging member being configured to obtain images therefrom through an outer surface of the biopsy sleeve, the handle being configured to removably engage the engagement member such that the biopsy sleeve is removably affixed to the imaging device to prevent translation along the longitudinal axis;
wherein the distal-most end of the elongate imaging member is positioned within one of the at least one lumen of the biopsy sleeve between the engagement member and the biopsy collector when the handle removably engages the engagement member; and
wherein during collection of the biopsy sample, the handle is configured to be selectively engaged with or disengaged from the engagement member of the biopsy sleeve.

2. The biopsy system of claim 1, wherein at least a portion of the biopsy sleeve is made of a transparent material that is configured to allow imaging therethrough by the imaging device.

3. The biopsy system of claim 1, wherein the biopsy sleeve includes a suction port configured to apply suction to tissue collected by the biopsy collector.

4. The biopsy system of claim 1, wherein the biopsy collector includes an opening into the lumen of the elongate shaft configured to receive tissue samples therethrough, wherein the opening has at least one tissue cutting means therein.

5. The biopsy system of claim 1, wherein the imaging device includes a complementary metal-oxide semiconductor fiberscope.

6. The biopsy system of claim 1, wherein the elongate imaging member includes optical fiber throughout the elongate imaging member configured to provide light for viewing.

7. The biopsy system of claim 6, wherein the imaging device includes an internal light source configured to transmit light down the optical fiber located within the elongate imaging member.

8. The biopsy system of claim 1, wherein the elongate shaft has at least two lumens extending therethrough, one of the lumens being configured to receive the elongate imaging member therein.

9. The biopsy system of claim 1, wherein the elongate shaft has a removable brush extending through the at least one lumen, the brush being configured to extend from the biopsy collector to collect tissue for the biopsy sample.

10. The biopsy system of claim 1, wherein when the handle removably engages the engagement member, the biopsy sleeve is configured to prevent a distal-most end of the elongate imaging member within the lumen from being aligned with or being positioned distally beyond the biopsy collector along the longitudinal axis.

11. The biopsy system of claim 1, wherein the biopsy sleeve has an angled distal portion protruding at a non-zero angle from the longitudinal axis.

12. A method of collecting a biopsy sample, comprising:
assembling a device for collecting the biopsy sample by removably engaging a biopsy sleeve with an imaging device by inserting an elongate imaging member that is internal with and extends distally from a handle of the imaging device directly into a lumen of the biopsy sleeve, the biopsy sleeve having proximal and distal ends with a longitudinal axis and the lumen extending therebetween, the biopsy sleeve having a biopsy collector positioned at or adjacent to the distal end thereof and an engagement member at the proximal end thereof, the elongate imaging member being inserted into the biopsy sleeve until a distal-most end of the elongate imaging member is positioned within the lumen of the bioopsy sleeve between the biopsy collector and the handle of the imaging device and until the engagement member engages the handle such that the biopsy sleeve is removably affixed to the imaging device to prevent translation along the longitudinal axis;
after assembling the device, inserting at least the biopsy collector of the biopsy sleeve and the distal-most end of the elongate imaging member into a uterus of a patient and positioning the biopsy collector adjacent to uterine tissue to be sampled using images taken by the elongate imaging member through an outer surface of the biopsy sleeve;
collecting a uterine tissue sample using the biopsy collector and the images taken by the elongate imaging member;
disengaging the biopsy sleeve from the imaging device by withdrawing the elongate imaging member from the biopsy sleeve; and
disposing of the biopsy sleeve while retaining the imaging device with the elongate imaging member.

13. The method of claim 12, further comprising applying suction to the biopsy collector by connecting a suction device to a suction port of the biopsy sleeve.

14. The method of claim 12, further comprising after collecting the tissue sample by the biopsy collector, removing the biopsy sleeve from the body cavity using images from the imaging device to guide removal.

15. The method of claim 12, wherein the elongate shaft of the biopsy sleeve has at least a second lumen therein, and the elongate imaging member is inserted into one of the two lumens.

16. The method of claim 12, further comprising, after positioning the biopsy sleeve adjacent to tissue, extending a removable brush from the biopsy collector to collect the tissue sample.

17. A method of collecting a biopsy sample, comprising:
assembling a device for collecting the biopsy sample by inserting an elongate imaging member that is integral with and extends distally from a handle of an imaging device into a lumen of a biopsy sleeve until a proximal end of the biopsy sleeve removably mates with the handle of the imaging device;

after assembling the device, inserting a biopsy collector on a distal portion of the biopsy sleeve and a distal end of the elongate imaging member into a uterus of a patient;

the distal-most end of the elongate imaging member being positioned within the lumen of the biopsy sleeve between the proximal end of the biopsy sleeve and the biopsy collector when the proximal end of the biopsy sleeve removably mates with the handle of the imaging device;

positioining the biopsy collector adjacent to uterine tissue to be collected using images taken by the elongate imaging member through an outer surface of the biopsy sleeve of the uterus during insertion and positioning;

collecting a uterine tissue sample using the biopsy collector and using the images taken by the elongate imaging member to guide collection of the biopsy collector;

disengaging the biopsy sleeve from the imaging device by withdrawing the elongate imaging member from the biopsy sleeve; and disposing of the biopsy sleeve while retaining the imaging device with the elongate imaging member.

18. The method of claim 17, wherein the proximal end of the biopsy sleeve removably mates with the handle of the imaging device such that the biopsy sleeve is removably, non-rotatably, and non-slidably affixed to the imaging device.

19. The method of claim 17, further comprising applying suction to the biopsy collector by connecting a suction device to a suction port of the biopsy sleeve.

20. The method of claim 17, wherein the biopsy sleeve has at least a second lumen therein, and the elongate imaging member is inserted into one of the two lumes.

21. The method of clim 17, further comprising, after positioning the biopsy sleeve adjacent to tissue, extending a removable brush from the biopsy collevtor to collect the tissue sample.

22. The method of claim 17, wherein the biopsy sleeve comprises only optically clear material.

23. A biopsy system, comprising:

a biopsy sleeve including an elongate shaft having a longitudinal axis, distal and proximal ends, and at least one lumen extending therebetween, the biopsy sleeve having an engagement member positioined on the proximal end of the elongate shaft, and the biopsy sleeve having a biopsy collector positioined adjacent to the distal end of the elongate shaft and configured to collect uterine tissue for a uterine biopsy sample; and an imaging device including a handle and an elongate imaging member integral therewith and extending distally from the handle, the elongate imaging member being configured to be inserted into and removed from the lumen of the elongate shaft of the biopsy sleeve, the elongate imaging member being configured to obtain images therefrom through an outer surface of the biopsy sleeve, the handle being configured to removably engage the engagement member such that the biopsy sleeve is removably affixed to the imaging device to prevent translation along the longitudinal axis;

wherein when the handle removably engages the engagement member, the distal-most end of the elongate imaging member is positioned within one of the at least one lumen of the biopsy sleeve between the engagement member and the biopsy collector; and wherein during collection of the biopsy sample, the handle is configured to be selectively engaged with or disengaged from the engagement member of the biopsy sleeve.

24. The biopsy system of claim 23, wherein at least a portion of the biopsy sleeve is made of a transparent material that is configured to allow imaging therethrough by the imaging device.

25. The biopsy system of claim 23, wherein the biopsy sleeve includes a suction port configured to apply suction to tissue collected by the biopsy collector.

26. The biopsy system of claim 23, wherein teh biopsy collector includes an opening into the lumen of the elongate shaft configured to receive tissue samples therethrough, wherein the opening has at least one tissue cutting means therein.

27. The biopsy system of claim 23, wherein the imaging device includes a complementary metal-oxide semiconductor fiberscope, and the elongate imaging member includes optical fiber throughout the elongate imaging member configured to provide light for viewing.

28. The biopsy system of claim 23, wherein the elongate shaft has at least two lumens extending therethrough, one of the lumens being configured to receive the elongate imaging member therein.

29. The biopsy system of claim 23, wherein the elongate shaft has a removable brush extending through the at least one lumen, the brush being configured to extend from the biopsy collector to collect tissue for the biopsy sample.

30. The biopsy system of claim 23, wherein a distal-most end of the elongate imaging member is positioned within the lumen of the biopsy sleeve between the engagement member and the biopsy collector when the handle removably engages the engagement member.

31. The biopsy system of claim 23, wherein the biopsy sleeve has an andled distal portion protruding at a non-zero angle from the longitudinal axis.

* * * * *